United States Patent [19]

Garza et al.

[11] Patent Number: 4,665,918
[45] Date of Patent: May 19, 1987

[54] PROSTHESIS SYSTEM AND METHOD

[76] Inventors: Gilbert A. Garza, 1236 15th St., Huntington, W. Va. 25701; Marek Kacki, 2412 Richmond Rd., Apt. #415, Lexington, Ky. 40502

[21] Appl. No.: 816,399

[22] Filed: Jan. 6, 1986

[51] Int. Cl.⁴ ............................................. A61M 29/02
[52] U.S. Cl. ...................................... 128/343; 128/344; 128/348.1; 623/1; 623/12
[58] Field of Search ............ 128/341, 343, 344, 348.1, 128/334 R; 623/1, 12

[56] References Cited

U.S. PATENT DOCUMENTS

| 3,713,175 | 1/1973 | Weisman | 623/1 X |
| 4,130,904 | 12/1978 | Whalen | 623/1 |
| 4,306,318 | 12/1981 | Mano et al. | 623/1 |
| 4,479,497 | 10/1984 | Fogarty et al. | 128/348.1 X |
| 4,503,569 | 3/1985 | Dotter | 623/1 |
| 4,573,470 | 3/1986 | Samson et al. | 128/344 |
| 4,582,181 | 4/1986 | Samson | 128/348.1 |

Primary Examiner—Albert J. Makay
Assistant Examiner—Steven E. Warner
Attorney, Agent, or Firm—Duckworth, Allen, Dyer

[57] ABSTRACT

A system and method is disclosed for implanting a prosthesis the length of a blood vessel. A generally tubular prosthesis member having an unobstructed central passageway is provided. The member contracts to a smaller dimension for delivery through the unobstructed portion of the length of blood vessel, and is outwardly expansible in the blood vessel. The prosthesis member is positioned in a contracted condition between a delivery catheter and an outer sheath, and expands outwardly responsive to removal of the sheath.

17 Claims, 22 Drawing Figures

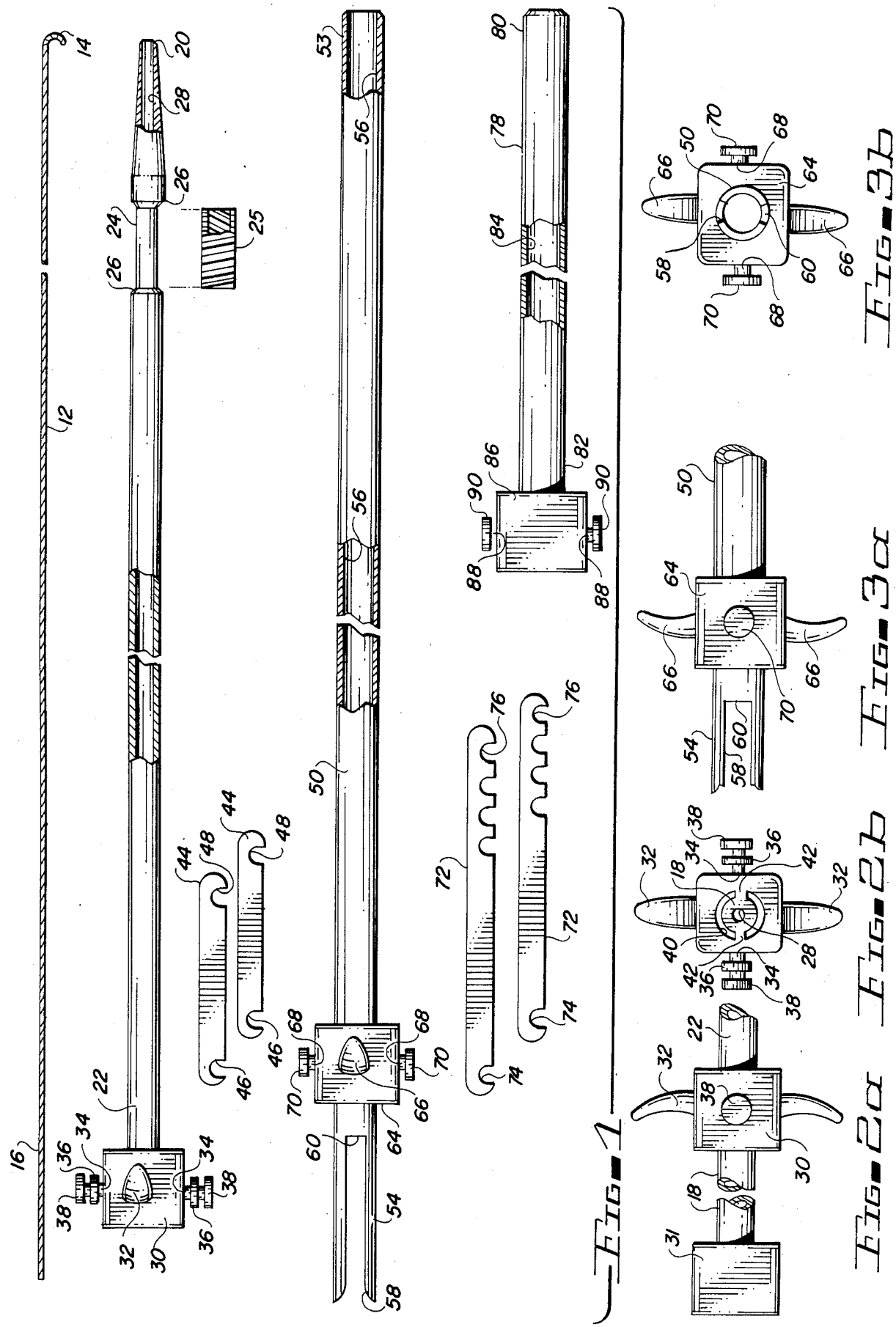

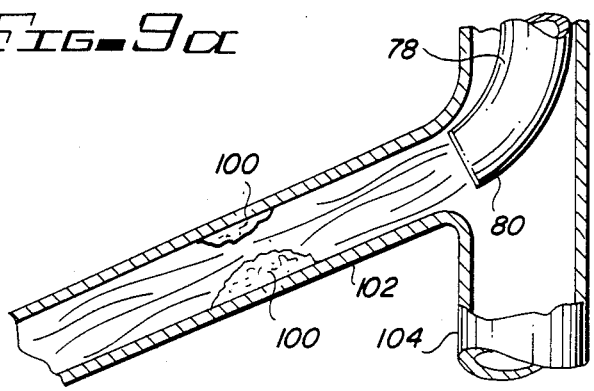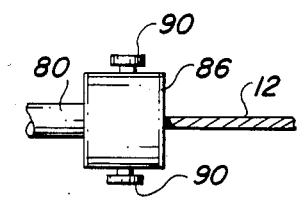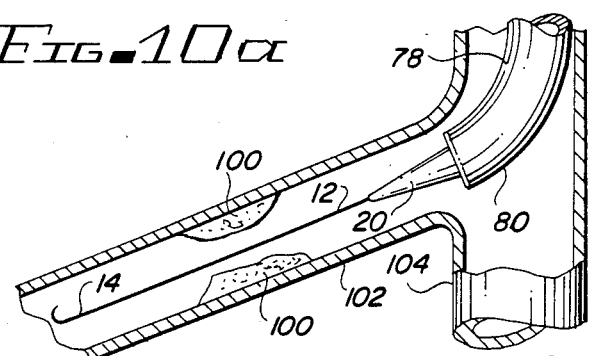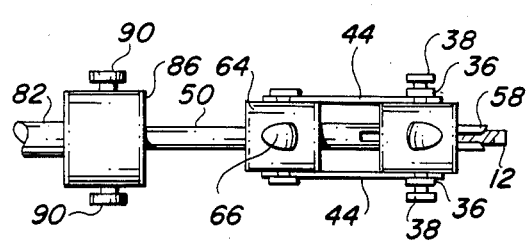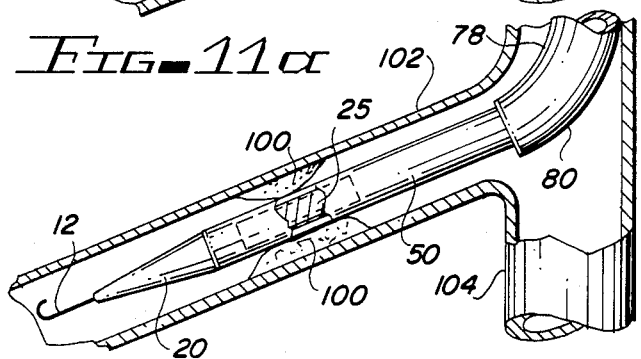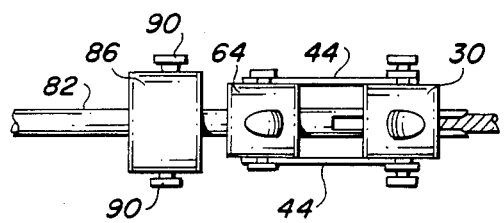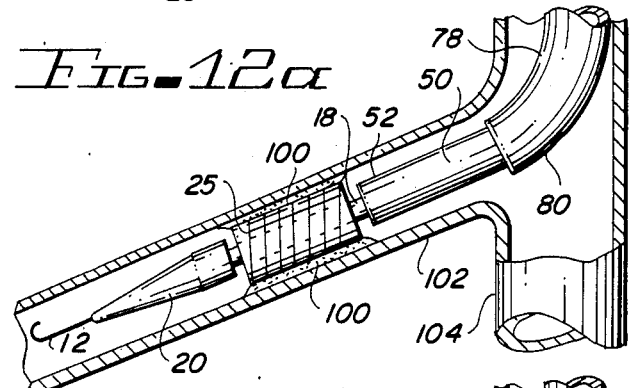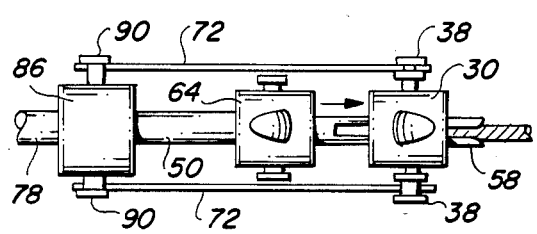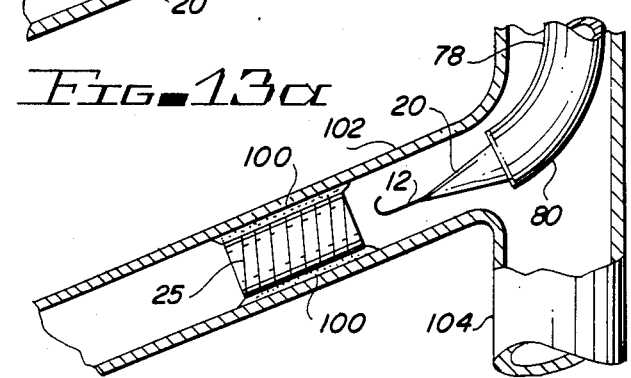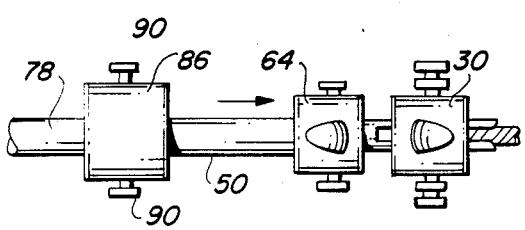

PROSTHESIS SYSTEM AND METHOD

BACKGROUND OF THE INVENTION

The present invention relates generally to prosthesis systems and methods for use in the human body, and specifically to such prosthesis systems and methods which are designed to overcome the effects of obstructions in blood vessels.

Arteriosclerosis is a disease which causes obstructions to develop in blood vessels, restricting the amount of blood which flows. This condition can be treated with a surgical bypass around the diseased portion of the vessel, or with a more recent technique known as balloon angioplasty, in which the obtruction is forced outwardly under pressure from an expansible balloon in a catheter system.

SUMMARY OF THE INVENTION

The present invention contemplates both a prosthesis system and method, as well as a delivery system and method, for the insertion of a prosthesis member into a cavity of a human body, and particularly in a blood vessel, in order to overcome the obstructions discussed above.

In accordance with a preferred embodiment of the present invention, the prosthesis member comprises a generally tubular member having an unobstructed central passageway and which is contractible to a storage condition for delivery into a blood vessel to be treated, and thereafter radially expandable so as to bear against the obstruction to increase the cross-sectional area of the blood vessel being treated.

The system and method further includes means for delivering the prosthesis member into the unobstructed center of the obstructed portion of the blood vessel and thereafter releasing the prosthesis member to expand outwardly against the obstruction. In the preferred embodiment, the delivery means includes a delivery catheter having a distal end dimensioned to pass through the unobstructed portion of the blood vessel with a portion of reduced wall thickness along its outer periphery to receive the prosthesis member in the contracted condition. The delivery means further include a sheath dimensioned to closely fit about the outer periphery of the delivery catheter, such that the contracted prosthesis member is positioned between the delivery catheter and the sheath. Upon movement of the sheath, generally caused by pulling away from the patient's body the proximal end of the sheath, the prosthesis member is released into the expanded condition and bears outwardly against the obstruction in the blood vessel.

In one embodiment, the generally tubular prosthesis member comprises a helical coil of an elastomeric material. In a second embodiment, the prosthesis member comprises a cylinder of expansible material having a generally longitudinal slot along the cylindrical wall thereof, with one edge of the cylinder along the slot overlapping the opposing edge of the slot in a contracted relationship when the cylinder is positioned between the delivery catheter and the sheath. When released, the overlapping edge expands outwardly, permitting the cylinder to bear against the obstruction.

The delivery system further includes means for guiding the prosthesis member to the length of blood vessel under treatment. The guiding means may include a central lumen in the delivery catheter adapted to receive a guidewire, and a guidewire of suitable dimension to fit therein. A guiding catheter is also provided, and fits about the outer periphery of the sleeve. Locking means for selectively locking the sheath with the delivery catheter, and the delivery catheter with the guiding catheter, is also provided at the proximal end of the two catheters and the sheath to hold the entire assembly together during insertion into the patient's body, and while positioning in the length of blood vessel under treatment.

DESCRIPTION OF THE DRAWINGS

For purposes of the drawings and the description of the preferred embodiment set forth below, the term "distal end" refers to that forward end of the prosthesis delivery system which extends into the human body. The term "proximal end" refers to that portion of the delivery system which is at the rearward end not extending into the human body, and which is used to manipulate the system so as to deliver the prosthesis to the desired location.

In the Drawings:

FIG. 1 is a top plan view of the prosthesis system of the present invention, which is dissembled to show the various components thereof. The various components are shown with a center portion broken away, and with portions in cross-section.

FIGS. 2A and 2B disclose, respectively, top plan and end views of the proximal end of a prosthesis delivery catheter in accordance with the preferred embodiment of the present invention.

FIGS. 3a and 3b disclose, respectively, top plan and end views of the proximal end of a sheath portion of the prosthesis delivery system in accordance with the preferred embodiment of the present invention.

FIGS. 9a, 10, 11a, 12a and 13a illustrate the distal end of the prosthesis system inserted within the circulatory system of a human body during successive steps in the utilization of the prosthesis system according to the present invention.

FIGS. 9b, 10b, 11b, 12b and 13b illustrate the proximal end of the prosthesis system during successive steps while inserting the prosthesis system into a human body in accordance with the present invention.

DESCRIPTION OF THE PREFERRED EMBODIMENT

Figure 4A:
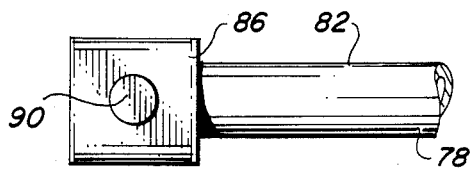
FIGS. 4a and 4b respectively illustrate the top plan and end views of the proximal end of a guiding catheter useful in the preferred embodiment of the present invention.

A description of the preferred embodiment of the present invention will be described with reference to the drawings.

Noting FIG. 1, the prosthesis delivery system of the present invention utilizes a conventional guidewire 12 having a "J" bend at the distal end 14, and a straight proximal end 16. The guidewire 12 has a lengthwise dimension sufficient to extend completely through the prosthesis delivery catheter 18, described next.

The prosthesis delivery catheter 18 has a tapered distal end 20 and a proximal portion 22 to which a hub 30 is connected. The prosthesis delivery catheter 18 also has a central lumen 28 that extends through the hub 30, the proximal portion 22 and along the entire length of the catheter 18 through the distal end 20. The central lumen 28 is dimensioned to receive the guidewire 12 and to permit the guidewire to slide through the lumen. A terminal hub 31 is coupled at the proximal end 23 of the delivery catheter 18, the hub 31 adapted for attachment to a pressure transducer.

The prosthesis delivery catheter 18 further includes a portion 24 near the distal end 20 having a reduced wall thickness about the peripheral dimension, the reduced wall thickness portion being approximately the same length as the prosthesis 25, described in greater detail below. The reduced wall thickness portion 24 is defined by tapered shoulders 26.

The hub 30 of the prosthesis delivery catheter 18 includes a pair of lock rods 34 extending from opposing sides of the hub 30, each locking rod including a pair of lock nobs 36 and 38 spaced from each other and the hub 30. A pair of finger grips 32 extend from opposing sides of the hub 30, and along a plane which is generally normal to the plane of the lock rods 34.

The hub 30 of the prosthesis delivery catheter 18 further includes a pair of slots 40 extending longitudinally through the hub and being curved to receive the distal extremities of a sheath 50. With specific reference to FIGS. 2b and 3a, the curved slots 40 are shown from the end view of the hub 30, and are spaced from each other by an area 42 of the hub. The proximal end 54 of the sheath 50 shown in FIG. 3a includes portions of the sheath 58 which are separated from each other by a slot 60 extending longitudinally through the proximal end 54 of the sheath 50. The separated portions 58 of the proximal end 54 of the sheath 50 are dimensioned to slide through the slots 40 of the hub 30 on the proximal end of the prosethesis delivery sheath 18 (FIG. 2b) when the sheath 50 is fitted along the prosthesis delivery catheter 18.

Figure 5:
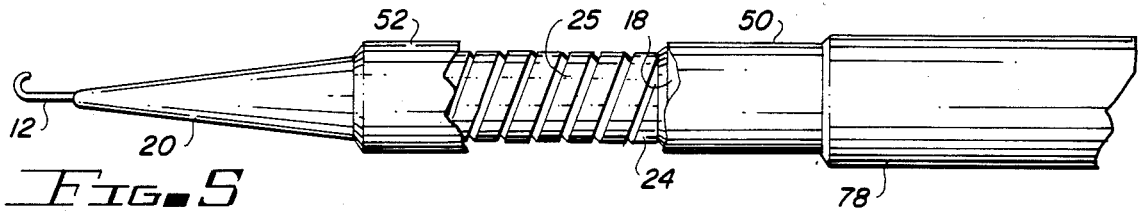
FIG. 5 is a top plan view of the distal end of the assembled prosthesis system of the preferred embodiment of the present invention, with a portion cut away for purposes of illustration.
Figure 6:
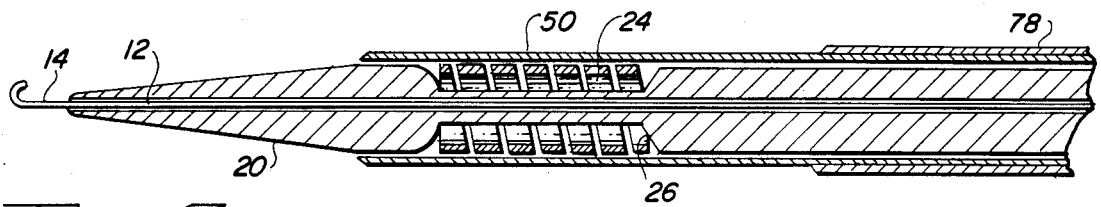
FIG. 6 illustrates the prosthesis delivery system shown in FIG. 5, with the various components thereof shown in cross-section.

Referring again to FIG. 1, the sheath 50 includes a distal end 52 and the proximal end 54 discussed earlier (the separated portions 58 and the slot 60 are also shown in FIG. 1). The sheath 50 includes a central lumen 56 dimensioned to fit over the outside periphery of the prosthesis delivery catheter 18. The central lumen 56 is also dimensioned to fit over the prosthesis 25 (FIG. 1) when the prosthesis is in a contracted condition within the portion of reduced wall thickness 24 of the catheter 18. This feature is shown in greater detail in FIGS. 5 and 6. As is shown, the prosthesis 25 comprises a coil of a nontoxic material capable of expansion and contraction, and dimensioned to fit between the prosthesis delivery catheter 18 in the reduced wall thickness portion 24 and the inside of the lumen 56 of the sheath 50 when in the contracted position, i.e. as is shown in FIGS. 5 and 6.

Reference is now made to FIGS. 1, 3a and 3b. The sheath 50 further includes a hub 64 along the distal end from the extremity of the slot 60. The hub 64 includes a pair of locking rods 68 extending from opposite sides of the hub 64 and lock nobs 70 at the extremity of each locking rod 68. A pair of finger grips 66 extend from opposing sides of the hub 64 along a plane with is generally perpendicular to the plane of the locking rods 68. Referring specifically to FIG. 1, a pair of locking arms 44 are provided, each locking arm having an indentation 46 along one end adapated to engage the locking rod 34 of the hub 30 at the proximal end 22 of the prosthesis delivery catheter 18. Similarly, each arm 44 includes another indentation adapted to engage the locking rod 68 of the hub 64 at the proximal end 54 of the sheath 50. The function and positioning of the locking arms 44 is described more fully below and is illustrated in an assembled condition in FIG. 7.

The prosthesis delivery system of the present invention further includes a guiding catheter 78 having a distal end 80 and a proximal end 82 to which a hub 86 is attached. The guiding catheter 78 further includes a central lumen 84 having an inner diameter sufficient to permit the sleeve 50 to be passed through the lumen 84.

Figure 4B:
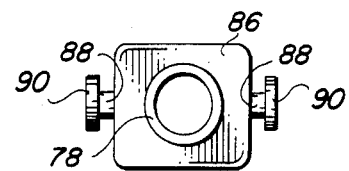
Figure 7:
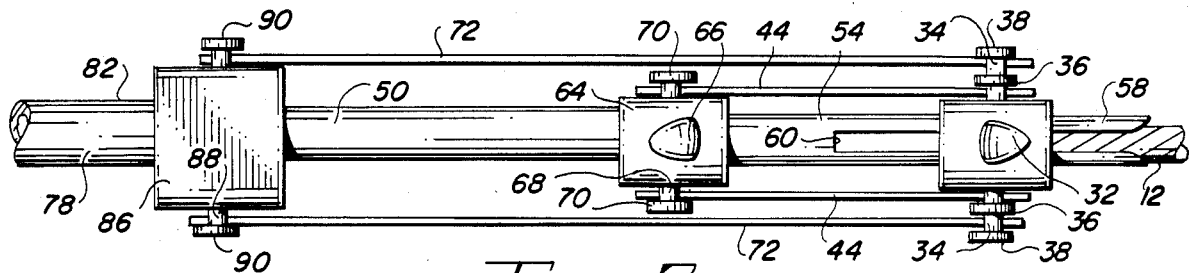
FIGS. 7 and 8 illustrate, respectively, the top plan and side views of the proximal end of the prosthesis system of the preferred embodiment, in an assembled condition.
Figure 8:
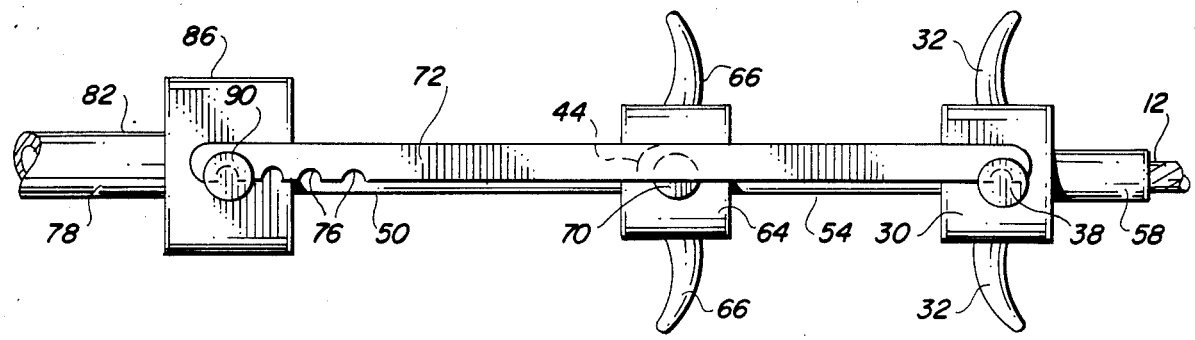

Referring to FIGS. 4a and 4b, the hub 86 of the guiding catheter 78 includes locking rods 88 with associated lock nobs 90 at the extremities thereof. Referring again to FIG. 1, a pair of locking arms 72 are provided, each locking arm including an indentation 74 at one end adapted to connect along the locking rod 34 of the hub 30 associated with the prosthesis delivery catheter 18, between the two lock nobs 36 and 38. The other end of each locking arm 72 includes a series of indentations 76, each of which is adapted to engage the locking rod 88 of the hub 86 associated with the guiding catheter 78. With reference to FIGS. 7 and 8, it can be seen that the locking arms 44 are dimensioned to maintain a specific distance between the hub 64 of the sheath 50 and the hub 30 of the prosthesis delivery catheter 18; and the locking arm 72 are adapted to permit selected distances to be maintained between the hub 86 of the guiding catheter 78, and the hub 30 of the prosthesis catheter 18.

The proximal ends of the assembled prosthesis delivery system of the present invention is also more fully depicted in FIGS. 7 and 8.

The manner of operation of the prosthesis system of the present invention and the related method will now be described with reference to FIGS. 9a-13b, inclusive.

In FIGS. 9a, 10a, 11a, 12a and 13a the reference numeral 100 refers to an obstruction in a blood vessel 102, which by way of example is shown as a branch of a major vessel 104. A typical example of where a vessel obstruction such as that shown at 100 in FIG. 9a would be the renal, femoral, popliteal, carotid and coronary arteries. However, this is referred to for reference purposes only, it being understood that the prosthesis system and method of the present invention is adapted for delivery of the prosthesis to virtually all obstructions in the circulatory system, and particularly those associated with the cardiovascular system.

Referring first to FIGS. 9a and 9b, the guiding catheter 78 is inserted into the circulatory system through a major vessel such as femoral artery by using the "J" guidewire 12. The guiding catheter 78 is manipulated through the circulatory system until the vessel 102 in question is reached. The "J" wire 12 is then twisted until access is made with the vessel 102 in question, turning the distal end 80 of the guiding catheter 78 in the direction of the vessel 102, using floroscopy and standard angiographic techniques. A base line angiogram is performed using a contrast solution passed through the guiding catheter 78, in order to identify and locate the obstruction 100.

The prosthesis delivery catheter 18, together with the prosthesis 25 and the covering sheath 50 are preassembled, and then passed through the guiding catheter 78 along the guidewire 12, with the guidewire being held steady while the catheter 18 is passed along the guidewire via the central lumen 28. Typically, the guidewire 12 has a standard diameter on the order of 0.038 inches. If the prosthesis 25 is to be delivered to a small diameter vessel such as a coronary artery, then a second guidewire on the order of 0.016 inches replaces the first guidewire after the guiding catheter-sheath combination has been directed to the smaller vessel. In FIG. 10a, the distal end 20 of the prosthesis delivery catheter 18 is shown exiting the distal end 80 of the guiding catheter 78. Referring to FIG. 10b, the combination of the sheath 50 and the prosthesis delivery catheter 18 are held in a fixed position via the locking arms 44 connected between the locking rods 34 of the catheter 18 and locking rods 68 of the sheath 50.

Reference is now made to FIG. 11a. The prosthesis delivery catheter 18 and sheath 50 combination are then pushed further along the "J" wire 12 until, as detected by floroscopy, the portion of reduced wall thickness 24 of the catheter 18 is passed through the unobstructed portion of reduced cross-sectional area inside the obstruction 100. Noting FIG. 11b, the advanced relationship between the hub 64 of the sheath 50 and the hub 86 of the guiding catheter 78 can be seen.

Reference is now made to FIGS. 12a and 12b. As is shown in FIG. 12b, as a next step, the locking arms 44 between the hub 64 of the sheath 50 and the hub 30 of the prosthesis delivery catheter 18 may be removed. Thereafter, the locking arms 72 are fixed between the hub 86 of the guiding catheter 78 and the hub 30 of the prosthesis delivery catheter 18. Next, the sheath 50 is pulled toward the hub 30 of the catheter 18 by using the finger grips 66 and 32. This causes the distal end 52 of the sheath 50 to pull away from and uncover the portion of reduced wall thickness 24 of the catheter 18, releasing the helical coil prosthesis 25, causing the prosthesis to expand outwardly against the obstruction 100. In the expanded condition, the prosthesis 25 thus forms a central, unobstructed passageway for the continued flow of blood through the vessel 102.

Referring now to FIGS. 13a and 13b, the locking arms 72 may now be removed from between the guiding catheter 78 and the prosthesis delivery catheter 18, permitting the entire assembly to be withdrawn, but leaving the prosthesis 25 in place to open the area of previously reduced cross-section in the vessel 102, thereby increasing the blood flow through that vessel. The guiding catheter 78, the sheath 50, the prosthesis delivery catheter 18 and the "J" wire 12 may then all be removed.

Figure 14:
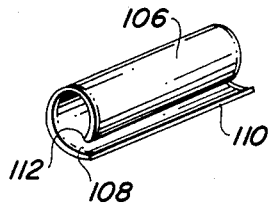
FIG. 14 illustrates an alternative embodiment of the prosthesis of the present invention.

An alternative embodiment for the prosthesis in accordance with the present invention is shown in FIG. 14. In this embodiment, the prosthesis 106 is formed of a cylinder of expansible, nontoxic material having a generally longitudinal slot 108 along the cylindrical wall thereof. An edge 110 of the cylindrical prosthesis 106 along the slot 108 overlaps and is spaced from the opposing edge 112 of the slot in a contracted relationship when the cylinder is positioned between the prosthesis guiding catheter 18 and the sheath 50. Upon release of the sheath 50 as described above, the prosthesis 106 springs outwardly to compress the obstruction 100, thereby opening the obstruction of the vessel, in a manner similar to the prosthesis 25 described above.

The prosthesis 25 and 106 may be made of surgical steel, teflon or any other appropriate nontoxic, nonthrombogenic material. While a helical coil and an expansible cylinder arrangement are shown in the drawings and described above, it will be understood that any independent and releasable prosthesis capable of expanding in a vessel and which may be delivered in the manner described above, is suitable.

Other modifications are also within the spirit and scope of the present invention. For example, while a specific means and method for locking the catheters and sheath together is described, it will be understood that other means including hand manipulation may be utilized to achieve the dimensional relationship between the catheter and the sheath during the functioning of the delivery system.

We claim:

1. A prosthesis system for insertion in a cavity of a human body, said system comprising:
   (a) a prosthesis delivery catheter dimensioned to pass into said body cavity;
   (b) a sheath dimensioned to closely fit about said catheter;
   (c) a prosthesis for implanting in said cavity, said prosthesis comprising a cylinder of resilient expansible material having a generally longitudinal slot along the cylindrical wall thereof, one edge of said cylinder along said slot overlapping the opposing edge of said slot in a contracted relationship when said cylinder is positioned between said catheter and said sheath, and expansible into said cavity responsive to removal of said sheath; and wherein
   (d) said prosthesis may be left in place in said body cavity after removal of said catheter and sheath.

2. The prosthesis system recited in claim 1 wherein said prosthesis comprises a coil of an elastomeric material.

3. The prosthesis system recited in claim 1 wherein said catheter includes a peripheral portion of reduced wall thickness adjacent a distal end thereof dimensioned to receive said prosthesis when contracted.

4. The prosthesis system recited in claim 1 further comprising:
   (a) said catheter including a central lumen dimensioned to receive a guidewire; and
   (b) a guidewire dimensioned to pass along said central lumen, wherein said guidewire may be positioned in said cavity and said catheter thereafter passed into said cavity by extending an outer extremity of said guidewire into said central lumen and pushing said catheter along said guidewire.

5. The prosthesis system recited in claim 1 further comprising means for selectively locking said sheath with said catheter until positioned in a desired manner within said body cavity.

6. The prosthesis system recited in claim 5 further comprising a guiding catheter having a central lumen dimensioned to receive said sheath.

7. The prosthesis system recited in claim 6 further comprising means for selectively locking said guiding catheter with said prosthesis delivery catheter-sheath combination, to prevent relative movement therebetween.

8. The prosthesis system recited in claim 7 wherein said means for selectively locking said catheters and sheath together comprises:

(a) a locking hub on said prosthesis delivery catheter at a proximal end which is opposite said distal end thereof;
(b) a locking hub on said sheath at a proximal end thereof adjacent said proximal end of said delivery catheter;
(c) a locking hub on said guiding catheter at a proximal end thereof adjacent said proximal end of said sheath;
(d) a locking arm between said delivery catheter hub and said sheath hub; and
(e) a locking arm between said delivery catheter hub and said guiding catheter hub.

9. A system for implanting a permanent prosthesis in a blood vessel for expanding a length of said blood vessel suffering a reduction in blood flow because of an obstruction therein, said system comprising:
(a) a prosthesis delivery catheter having a distal end dimensioned for extension into said blood vessel along said length of obstruction;
(b) a sheath having a distal end dimensioned for extension into said blood vessel along said length of obstruction and further dimensioned to fit about the outer periphery of said delivery catheter; and
(c) prosthesis means outwardly expandable against said obstruction to increase the cross-sectional area of said blood vessel, said prosthesis means formed of a material which contracts to fit between said delivery catheter and said sheath and which expands outwardly responsive to removal of said sheath, said prosthesis means resting against said delivery catheter when in a contracted position between said delivery catheter and said sheath, said prosthesis means being free of any connections to said delivery catheter and said sheath, permitting said prosthesis means to remain in said blood vessel after removal of said delivery catheter and said sheath, said prosthesis means comprising a cylinder of expansible material having a generally longitudinal slot along the cylindrical wall thereof, one edge of said cylinder being spaced from the opposing edge of said slot in said contracted position when said cylinder is positioned between said delivery catheter and said sheath.

10. The system recited in claim 9 wherein said prosthesis means includes a generally tubular member having an unobstructed central passageway.

11. The system recited in claim 9 wherein said prosthesis means comprises a coil of an elastomeric material.

12. The system recited in claim 9 wherein said delivery catheter includes a peripheral portion of reduced wall thickness along said distal end thereof dimensioned to receive said prosthesis when in the contracted position.

13. A system for implanting a prosthesis in a length of blood vessel having an unobstructed portion of reduced cross-sectional area caused by an obstruction along the walls of said length of blood vessel, said system comprising:
(a) a prosthesis member having an unobstructed central passageway, said prosthesis member being outwardly expansible against said obstruction to increase the cross-sectional area of said blood vessel and contractable to permit movement through said unobstructed portion of said length of blood vessel, said prosthesis comprising a cylinder of resilient expansible material having a generally longitudinal slot along the cylindrical wall thereof, one edge of said cylinder along said slot overlapped with the opposing edge of said slot in a contracted relationship when said cylinder is positioned between said catheter and said sheath; and
(b) means for holding said prosthesis in a contracted position and for delivering said prosthesis means into said unobstructed portion of said blood vessel and releasing said prosthesis member to expand outwardly against said obstruction.

14. The prosthesis recited in claim 13 wherein said delivery means includes a sheath dimensioned to fit about said prosthesis member when in the contracted position, said prosthesis member expanding responsive to movement of said sheath.

15. The system recited in claim 14 wherein said delivery means includes a delivery catheter having a distal end dimensioned to pass through said unobstructed portion of said blood vessel, said delivery catheter having a portion of reduced wall thickness along said distal end for receiving said prosthesis member when contracted.

16. The system recited in claim 15 further comprising:
(a) said delivery catheter including a central lumen dimensioned to receive a guidewire;
(b) a guidewire dimensioned to pass along said central lumen; and
(c) a guiding catheter having a central lumen dimensioned to receive said sheath.

17. A method for implanting a prosthesis in a length of blood vessel having an unobstructed portion of reduced cross-sectional area caused by an obstruction along the walls of said length of blood vessel, said method comprising the steps of:
(a) providing a prosthesis member having an unobstructed central passageway, said prosthesis member being contractible to a contracted position and outwardly expansible so as to bear against the obstruction of said blood vessel to increase the cross-sectional area thereof, said prosthesis comprising a cylinder of expansible material having a generally longitudinal slot along the cylindrical wall thereof, one edge of said cylinder along said slot overlapping the opposing edge of said slot in said contracted position;
(b) contracting said prosthesis member;
(c) delivering said contracted prosthesis member into said unobstructed portion of said blood vessel; and thereafter
(d) releasing said prosthesis member from said contracted position to expand outwardly against said obstruction.

* * * * *